(12) United States Patent
Hayashi et al.

(10) Patent No.: US 10,743,760 B2
(45) Date of Patent: Aug. 18, 2020

(54) OPHTHALMOLOGICAL DEVICE AND OPHTHALMOLOGICAL INSPECTION SYSTEM

(71) Applicant: TOPCON CORPORATION, Itabashi-ku (JP)

(72) Inventors: Takefumi Hayashi, Wako (JP); Kouta Fujii, Toda (JP)

(73) Assignee: TOPCON CORPORATION, Itabashi (JP)

( * ) Notice: Subject to any disclaimer, the term of this patent is extended or adjusted under 35 U.S.C. 154(b) by 69 days.

(21) Appl. No.: 16/066,157

(22) PCT Filed: Jan. 13, 2017

(86) PCT No.: PCT/JP2017/001100
§ 371 (c)(1),
(2) Date: Jun. 26, 2018

(87) PCT Pub. No.: WO2017/135016
PCT Pub. Date: Aug. 10, 2017

(65) Prior Publication Data
US 2019/0008380 A1    Jan. 10, 2019

(30) Foreign Application Priority Data
Feb. 4, 2016   (JP) .................... 2016-019389

(51) Int. Cl.
*A61B 3/103* (2006.01)
*A61B 3/12* (2006.01)
(Continued)

(52) U.S. Cl.
CPC ............... *A61B 3/103* (2013.01); *A61B 3/10* (2013.01); *A61B 3/102* (2013.01); *A61B 3/117* (2013.01); *A61B 3/12* (2013.01)

(58) Field of Classification Search
CPC ...... A61B 3/00; A61B 3/09; A61B 3/10; A61B 3/103; A61B 3/102; A61B 3/12;
(Continued)

(56) References Cited

U.S. PATENT DOCUMENTS

2009/0185136 A1    7/2009  Isogai et al.
2011/0128498 A1    6/2011  Nakamura
(Continued)

FOREIGN PATENT DOCUMENTS

JP    2006-187482 A    7/2006
JP    2011-115300 A    6/2011
(Continued)

OTHER PUBLICATIONS

Japanese Office Action dated Aug. 7, 2019 in Japanese Application No. 2016-019389.
(Continued)

*Primary Examiner* — Jie Lei
(74) *Attorney, Agent, or Firm* — Xsensus LLP

(57) ABSTRACT

An ophthalmological device according to the embodiments comprises an objective lens, an objective measurement optical system, an interference optical system, and an image forming unit. The objective measurement optical system irradiates light onto a subject's eye via the objective lens and detects returning light from the subject's eye. The interference optical system splits light from a light source into reference light and measurement light, projects the measurement light onto the subject's eye via the objective lens so as to overlap at least part of an area of the irradiated light at the subject's eye by the objective measurement optical system, generates interference light between returning light of the measurement light and the reference light, and detects the generated interference light. The image forming unit forms a tomographic image of the subject's eye based on a
(Continued)

detection result of the interference light by the interference optical system.

11 Claims, 10 Drawing Sheets

(51) Int. Cl.
*A61B 3/10* (2006.01)
*A61B 3/117* (2006.01)

(58) Field of Classification Search
CPC ..... A61B 3/117; A61B 3/1173; A61B 3/0025; A61B 3/14; G06K 9/00
USPC ....... 351/205, 206, 208, 210–212, 216, 221, 351/246, 236; 356/479, 497, 498; 382/131
See application file for complete search history.

(56) References Cited

U.S. PATENT DOCUMENTS

| | | |
|---|---|---|
| 2011/0170062 A1 | 7/2011 | Isogai et al. |
| 2012/0083667 A1* | 4/2012 | Isogai ............... A61B 3/102 600/300 |
| 2012/0127428 A1 | 5/2012 | Isogai et al. |
| 2014/0300863 A1* | 10/2014 | Fukuma ............... A61B 3/12 351/206 |
| 2014/0300864 A1 | 10/2014 | Fukuma et al. |
| 2014/0300866 A1 | 10/2014 | Fukuma et al. |
| 2014/0320809 A1 | 10/2014 | Fukuma et al. |
| 2014/0320810 A1 | 10/2014 | Fukuma et al. |
| 2015/0320308 A1 | 11/2015 | Akiba et al. |

FOREIGN PATENT DOCUMENTS

| | | |
|---|---|---|
| JP | 2014-128306 A | 7/2014 |
| JP | 2014-200679 A | 10/2014 |
| JP | 2015-128630 A | 7/2015 |

OTHER PUBLICATIONS

English Translation of International Search Report issued for PCT/JP2017/001100 dated Feb. 14, 2017.

* cited by examiner

OPHTHALMOLOGICAL DEVICE AND OPHTHALMOLOGICAL INSPECTION SYSTEM

CROSS-REFERENCE TO RELATED APPLICATIONS

This application is a national stage (under 35 U.S.C. 371) of International Patent Application No. PCT/JP2017/001100, filed Jan. 13, 2017, claiming priority to Japanese Patent Application No. 2016-019389, filed Feb. 4, 2016, both of which are herein incorporated by reference in their entirety.

FIELD

Embodiments according to the present invention relates to an ophthalmological device and an ophthalmological inspection system.

BACKGROUND

Ophthalmological devices capable of performing an objective measurement for a subject's eye are known. For example, 1 Japanese Unexamined Patent Application Publication No. 2006-187482 discloses an ophthalmological device that obtains a spherical power, an astigmatic power, and an astigmatic axis angle of the subject's eye, by analyzing a ring image acquired by projecting a ring-shaped light flux for measuring an ocular refractive power onto a fundus of the subject's eye and detecting returning light thereof.

However, in case that a diseased site exists on the fundus of the subject's eye, when the ring-shaped light flux for measuring is projected onto the diseased site, distortion or deformation of the shape of the ring image acquired by detecting the returning light from the fundus increases. Thereby, there is a problem that the accuracy of the obtained spherical power, astigmatic power, and astigmatic axis angle of the subject's eye decreases. Such variations in objective measurement values may also influence the accuracy of subjective inspection performed by reflecting the objective measurement values.

Further, the distortion of the shape of the ring image and the like may be caused not only by the diseased site of the fundus but also by the ocular media including a crystalline lens. Therefore, it is sometimes impossible to specify the reason why the accuracy of the obtained spherical power, astigmatic power, and astigmatic axis angle of the subject's eye decreases, merely by analyzing the ring image.

An ophthalmological device according to embodiments comprises an objective lens, an objective measurement optical system, an interference optical system, and an image forming unit. The objective measurement optical system irradiates light onto a subject's eye via the objective lens and detects returning light from the subject's eye. The interference optical system splits light from a light source into reference light and measurement light, projects the measurement light onto the subject's eye via the objective lens so as to overlap at least part of an area of the irradiated light at the subject's eye by the objective measurement optical system, generates interference light between returning light of the measurement light and the reference light, and detects the generated interference light. The image forming unit forms a tomographic image of the subject's eye based on a detection result of the interference light by the interference optical system.

An ophthalmological inspection system according to the embodiments comprises a left inspection unit for inspecting the subject's left eye and a right inspection unit for inspecting the subject's right eye, wherein at least one of the left inspection unit and the right inspection unit includes the ophthalmological device according to the embodiments.

With an ophthalmological device and an ophthalmological inspection system according to the embodiments, accuracy of an objective measurement value can be improved.

DESCRIPTION OF THE EMBODIMENTS

Figure 1:
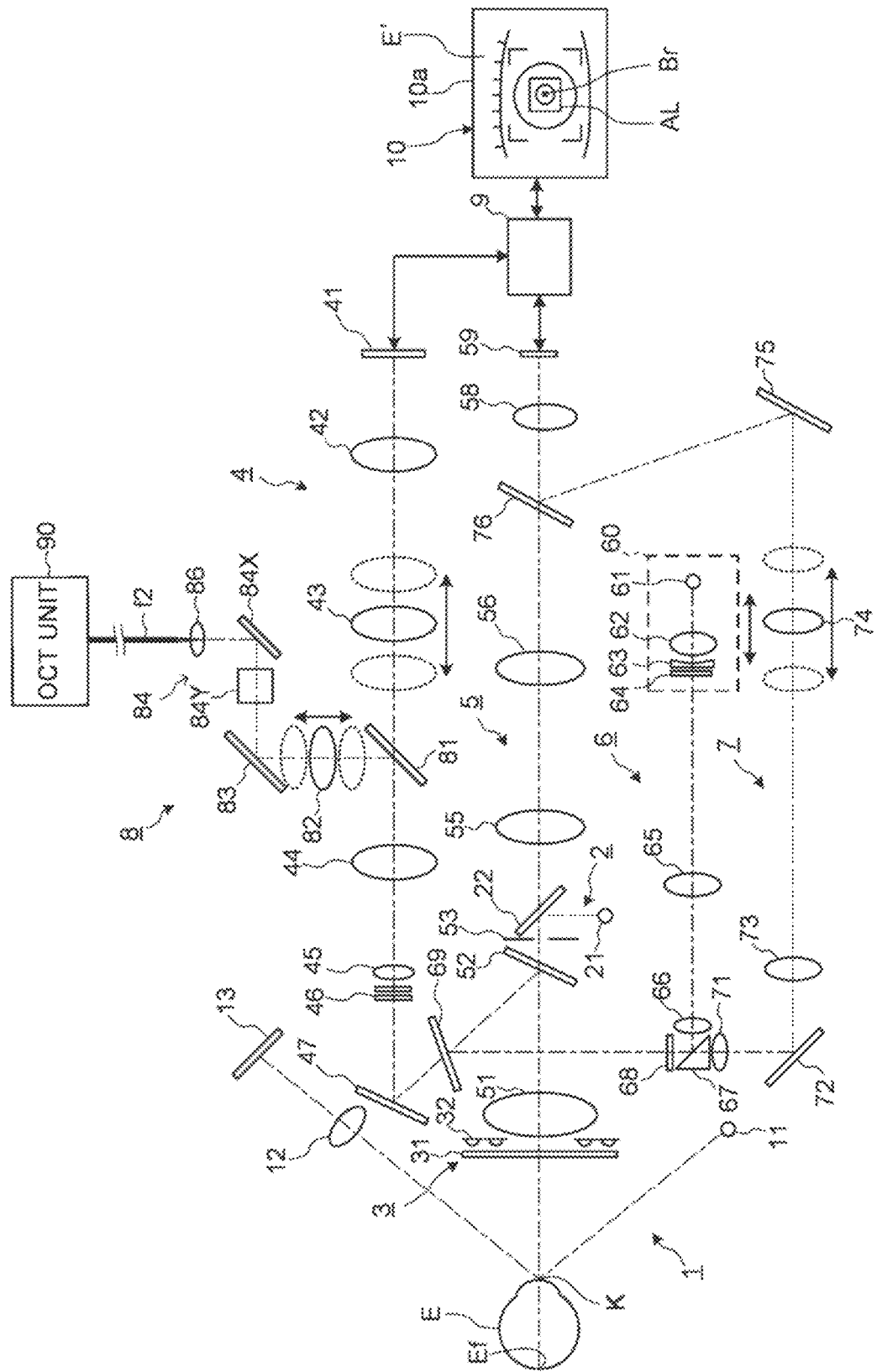
FIG. 1 is a schematic diagram illustrating an example of a configuration of an optical system of an ophthalmological device according to embodiments.

Referring now to the drawings, a description is given of an ophthalmological device and an ophthalmological inspection system according to embodiments. The disclosure of the references cited in this specification may be incorporated herein by reference.

<Ophthalmological Device>

An ophthalmological device according to embodiments is capable of performing at least one of arbitrary subjective inspections and arbitrary objective measurements. In the subjective inspections, information (visual targets or optotypes, etc.) is presented to a subject, and the result is obtained based on a response to the information from the subject. Examples of the subjective inspections include a visual field test, and subjective refractivity measurement such as a far vision test, a near vision test, a contrast test, a glare test and the like. In the objective measurements, light is projected onto the subject's eye and information on the subject's eye is acquired based on a detection result of returning light thereof. The objective measurements include a measurement for acquiring the characteristics of the subject's eye and an imaging for acquiring an image of the subject's eye. Examples of the objective measurements include objective refractivity measurement, corneal shape measurement, intraocular pressure measurement, fundus photographing, tomographic imaging using optical coherence tomography (hereinafter, OCT) (OCT imaging), measurement using OCT, and the like.

Hereinafter, a case is considered in which the ophthalmological device according to the embodiments is capable of performing the far vision test, the near vision test and the like as the subjective inspection, and is also capable of performing the objective refractivity measurement, the corneal shape measurement, the OCT imaging and the like as the objective measurement. However, the configuration of the ophthalmological device according to the embodiments is not limited to this.

Further, the case of using the Fourier domain OCT method will be described in the OCT imaging. In particular, the ophthalmological device according to the following embodiments is capable of performing OCT imaging using the spectral domain OCT method. For the OCT imaging, a type other than the spectral domain (for example, a swept source OCT method) may be used. The time domain OCT method may be employed in the OCT imaging of the following embodiments.

<Configuration>

The ophthalmological device according to the embodiments includes a face support unit fixed to a base and a stage movable in front, back, left, and right directions with respect to the base. The stage is provided with a head unit in which an optical system for performing inspection (measurement) of the subject's eye is housed. The face support unit and the head unit can be relatively moved by operating with respect to an operation unit provided on the side of an examiner. Further, in the ophthalmological device, the face support unit and the head unit can be relatively moved automatically by performing alignment described after.

Figure 2:
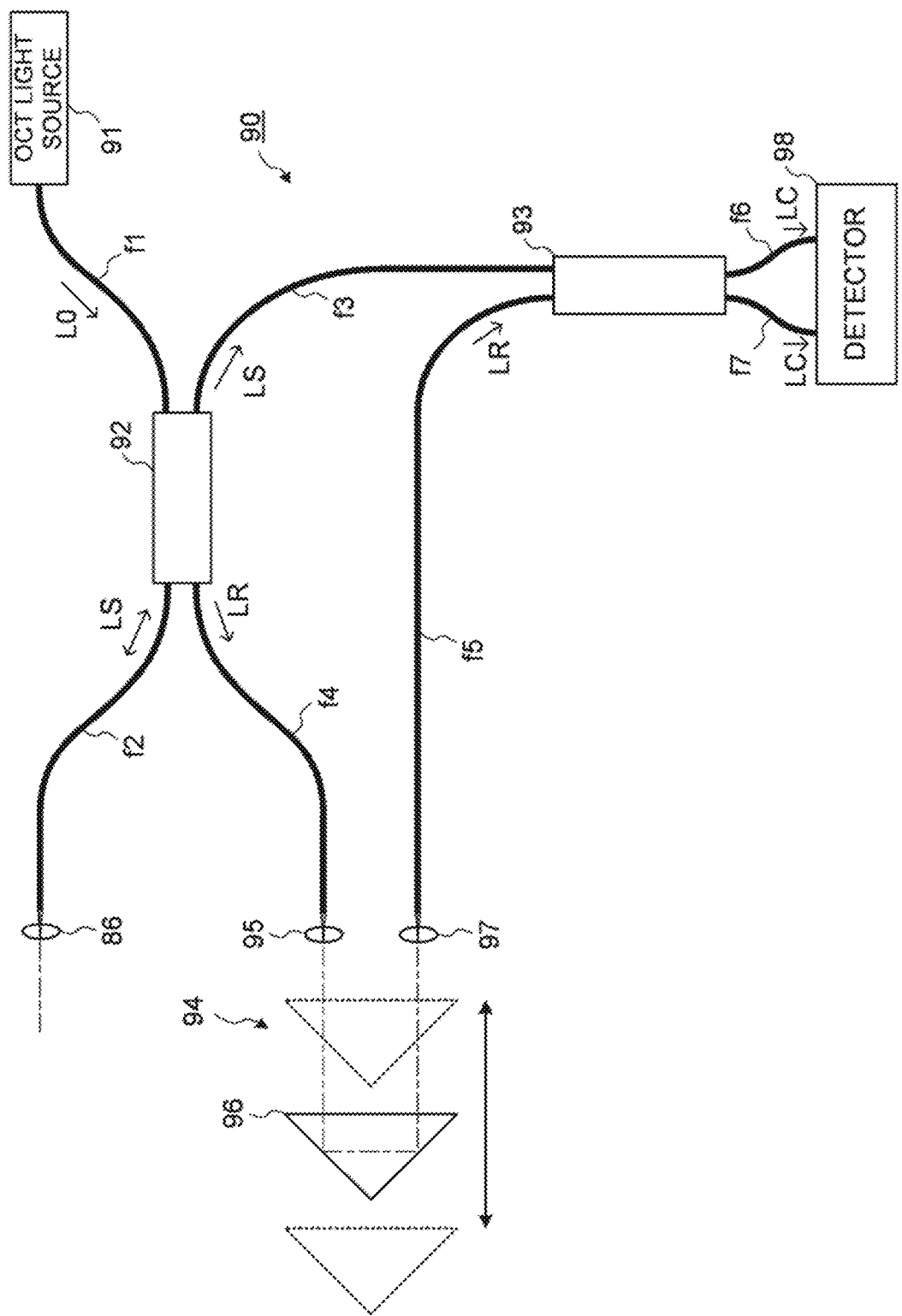
FIG. 2 is a schematic diagram illustrating an example of the configuration of the optical system of the ophthalmological device according to the embodiments.
Figure 3:
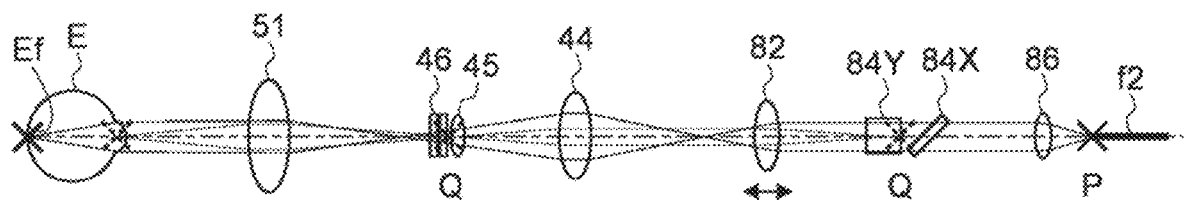
FIG. 3 is a schematic diagram illustrating an example of the configuration of the optical system of the ophthalmological device according to the embodiments.

FIGS. 1 to 3 illustrate an example of the configuration of the optical system of the ophthalmological device according to the embodiments. The ophthalmological device includes, as an optical system for performing inspections of the subject's eye E, a Z alignment system 1, an XY alignment system 2, a keratometry system 3, a visual target projection system 4, an observation system 5, a refractometry projection system 6, a refractometry light reception system 7, and an OCT optical system 8. In addition, the ophthalmological device includes a processing unit 9.

(Processing Unit 9)

The processing unit 9 controls each part of the ophthalmological device. Further, the processing unit 9 is capable of performing various types of arithmetic processing. The processing unit 9 includes a processor. The function of the processor is implemented by a circuit(s) such as, for example, a CPU (central processing unit), a GPU (graphics processing unit), an ASIC (application specific integrated circuit), and a PLD (programmable logic device). Examples of PLD include a simple programmable logic device (SPLD), a complex programmable logic device (CPLD), and a field programmable gate array (FPGA). The processing unit 9 realizes the function according to the embodiments, for example, by read out a computer program stored in a storage circuit or a storage device and executing the computer program.

(Observation System 5)

The observation system 5 is configured to acquire a moving image of an anterior ocular segment of the subject's eye E. Returning light (infrared light) from the anterior ocular segment of the subject's eye E passes through an objective lens 51, penetrates a dichroic mirror 52, and passes through an opening of a diaphragm 53. The light passing through the opening of the diaphragm 53 penetrates a half mirror 22, passes through relay lenses 55 and 56, and penetrates a half mirror 76. The light penetrating the half mirror 76 forms an image on an imaging surface of an imaging element 59 (area sensor) by an imaging lens 58. The imaging element 59 performs an imaging and a signal outputting at a predetermined rate. The output (video signal) of the imaging element 59 is input to the processing unit 9. The processing unit 9 displays an anterior ocular segment image E' based on this video signal on a display screen 10a of a display unit 10. The anterior ocular segment image E' is an infrared moving image for example. The observation system 5 may include an illumination light source for illuminating the anterior ocular segment.

(Z Alignment System 1)

The Z alignment system 1 is configured to project light (infrared light) for performing alignment in an optical axis direction (front-back directions, Z direction) of the observation system 5 onto the subject's eye E. Light emitted from a Z alignment light source 11 is irradiated onto a cornea K of the subject's eye E, is reflected by the cornea K, and forms an image on a line sensor 13 by an imaging lens 12. When the position of the apex of the cornea changes in the front-back directions, the projection position of the light onto the line sensor 13 changes. The processing unit 9 specifies a position of the apex of the cornea of the subject's eye E based on the projection position of the light onto the line sensor 13 and performs Z alignment based on this.

(XY Alignment System 2)

The XY alignment system 2 is configured to project light (infrared light) for performing alignment in a direction (left-right directions (X direction), up-down directions (Y direction)) orthogonal to the optical axis direction of the observation system 5 onto the subject's eye E. The XY alignment system 2 includes an XY alignment light source 21 disposed in an optical path which is branched from the observation system 5 by the half mirror 22. Light emitted from the XY alignment light source 21 is reflected by the half mirror 22 and is projected onto the subject's eye E through the observation system 5. Reflected light from the cornea K is guided to the imaging element 59 through the observation system 5.

An image (bright spot image) of the reflected light is included in the anterior ocular segment image E'. The processing unit 9 displays an alignment mark AL and the anterior ocular segment image E' including the bright spot image Br on the display screen 10a, as illustrated in FIG. 1. In the case of performing XY alignment manually, the examiner or a user such as the subject, or the like performs an operation for moving the optical system so as to guide the bright spot image Br in the alignment mark AL. In the case of performing XY alignment automatically, the processing unit 9 controls a mechanism for moving the optical system so as to cancel a displacement of the bright spot image Br with respect to the alignment mark AL.

(Keratometry System 3)

The keratometry system 3 is configured to project a ring-shaped light flux (infrared light) for measuring a shape of the cornea K onto the cornea K. A kerato plate 31 is disposed between the objective lens 51 and the subject's eye E. A kerato-ring light source 32 is provided on the back side (the objective lens 51 side) of the kerato plate 31. By illuminating the kerato plate 31 with light from the kerato-ring light source 32, the ring-shaped light flux is projected onto the cornea K. The reflected light (kerato-ring image) is detected by the imaging element 59 along with the anterior ocular segment image. The processing unit 9 calculates a corneal shape parameter, by performing a known calculation based on this kerato-ring image.

(Visual Target Projection System 4)

The visual target projection system 4 is configured to present various kinds of visual targets such as a fixation target and a visual target for a subjective inspection to the subject's eye E. A liquid crystal panel 41 displays a pattern representing a visual target under the control of the processing unit 9. Light (visible light) output from the liquid crystal panel 41 passes through a relay lens 42 and a focusing lens 43, and penetrates a dichroic mirror 81. The light penetrating the dichroic mirror 81 passes through a relay lens 44, a pupil lens 45, and a VCC lens 46, is reflected by a reflective mirror 47, penetrates a dichroic mirror 69, and is reflected by the dichroic mirror 52. The reflected light by the dichroic mirror 52 passes through the objective lens 51 and is projected onto a fundus Ef.

The focusing lens 43 is movable along an optical axis of the visual target projection system 4. The position of the focusing lens 43 is adjusted so that the liquid crystal panel 41 and the fundus Ef are optically conjugate with each other. The VCC lens 46 is capable of adjusting the astigmatism of the subject's eye (that is, the VCC lens 46 is capable of correcting the astigmatism of the subject's eye). In particular, the VCC lens 46 is capable of changing an astigmatic power and an astigmatic axis angle to be added to the subject's eye E and correcting at least the astigmatic power and the astigmatic axis angle among the ocular aberrations of the subject's eye under the control of the processing unit 9. Thereby, the astigmatic state of the subject's eye E is corrected.

The liquid crystal panel 41 is capable of displaying the pattern representing a fixation target for fixating the subject's eye E under the control of the processing unit 9. The fixation position is moved by changing the display position of the pattern representing the fixation target in the liquid crystal panel 41, thereby fixation can be induced. Further, the visual target projection system 4 may include a glare test optical system for projection glare light onto the subject's eye E along with the visual target described above.

In the case of performing the subjective inspection, the processing unit 9 controls the liquid crystal panel 41, the focusing lens 43, and the VCC lens 46 based on the result of the objective measurement. The processing unit 9 controls the liquid crystal panel 41 to display the visual target selected by the examiner or the processing unit 9. Thereby, the visual target is presented to the subject. The subject responses with respect to the visual target. Upon receiving input of the response contents, the processing unit 9 performs further control or calculates a subjective inspection value. For example, in the visual acuity measurement, the processing unit 9 selects a next visual target based on the response to the Landolt ring or the like, presents the next visual target to the subject's eye, and determines the visual acuity value by repeatedly performing this.

In the objective measurement (objective refractivity measurement, etc.), a landscape chart is projected on the fundus Ef. Alignment is performed while the subject stares at the landscape chart, and the refractive power of the subject's eye is measured in foggy vision.

(Refractometry Projection System 6 and Refractometry Light Reception System 7)

The refractometry projection system 6 and the refractometry light reception system 7 are used for the objective refractivity measurement (refractometry). The refractometry projection system 6 is configured to project a ring-shaped light flux (infrared light) for the objective measurement onto the fundus Ef. In this specification, the ring-shaped light flux includes a light flux with a part of the ring discontinued. The refractometry light reception system 7 is configured to receive returning light of the ring-shaped light flux from the subject's eye E.

A light source unit 60 includes a refractometry light source 61, a condenser lens 62, a conical prism 63, and a ring opening plate 64. The light source unit 60 is movable along an optical axis of the refractometry projection system 6. The refractometry light source 61 is located in a position optically conjugate with the fundus Ef. Light emitted from the refractometry light source 61 passed through the condenser lens 62, penetrates the conical prism 63, passes through a ring-shaped opening part of the ring opening plate 64, and becomes a ring-shaped light flux. The ring-shaped light flux formed by the ring opening plate 64 passes through a relay lens 65 and a pupil lens 66, is reflected by a reflective surface of a perforated prism 67, passes through a rotary prism 68, and is reflected by the dichroic mirror 69. The light reflected by the dichroic mirror 69 is reflected by the dichroic mirror 52, passes through the objective lens 51, and is projected onto the fundus Ef.

The rotary prism 68 is used for averaging the light quantity distribution of the ring-shaped light flux with respect to the blood vessel or the diseased site of the fundus Ef.

Returning light of the ring-shaped light flux projected onto the fundus Ef passes through the objective lens 51, and is reflected by the dichroic mirrors 52 and 69. The returning light reflected by the dichroic mirror 69 passes through the rotary prism 68, passes through a hole part of the perforated prism 67, passes through a pupil lens 71, and is reflected by a reflective mirror 72. The light reflected by the reflective mirror 72 passes through a relay lens 73 and a focusing lens 74, and is reflected by a reflective mirror 75. The light reflected by the reflective mirror 75 is reflected by a half mirror 76 and forms an image on the imaging surface of the imaging element 59 by the imaging lens 58. The processing unit 9 calculates a spherical power S, an astigmatic power C, and an astigmatic axis angle A of the subject's eye E by performing the known calculation based on the output of the imaging element 59.

The processing unit 9 controls the light source unit 60 and the focusing lens 74 to move respectively to positions where the refractometry light source 61, the fundus Ef, and the imaging element 59 are conjugate with each other, in the direction of the optical axis. Further, the processing unit 9 controls the focusing lens 43 to move in the optical axis in conjunction with the movement of the light source unit 60 and the focusing lens 74. In addition, the processing unit 9 may control a focusing lens 82 of the OCT optical system 8 to move in the optical axis in conjunction with the movement of the light source unit 60 and the focusing lens 74.

(OCT Optical System 8)

The OCT optical system 8 is an optical system for OCT imaging. The position of the focusing lens 82 is adjusted so that an end face of an optical fiber f2 and the fundus Ef are optically conjugate with each other based on the result of the refractometry performed before the OCT imaging.

An optical path of the OCT optical system 8 is coupled with an optical path of the visual target projection system 4 by the dichroic mirror 81. Thereby, the optical axes of the OCT optical system 8 and the visual target projection system 4 can be coupled coaxially.

The OCT optical system 8 includes an OCT unit 90. As illustrated in FIG. 2, in the OCT unit 90, like general swept-source-type OCT apparatuses, the OCT light source 91 includes a wavelength tunable type (a wavelength scanning type) light source capable of sweeping (scanning) the wavelengths of emitted light. The wavelength tunable type light source includes a laser light source that includes a resonator. The OCT light source 91 temporally changes the output wavelength in the near infrared wavelength band which cannot be visually recognized by the human eye.

Light (infrared light, broadband light) LO output from the OCT light source 91 is guided through an optical fiber f1 to a fiber coupler 92, and divided into measurement light LS and reference light LR. The measurement light LS is guided to a collimator lens 86 through an optical fiber f2. On the other hand, the reference light LR is guided to a reference optical path length changing unit 94 through an optical fiber f4.

The reference optical path length changing unit 94 changes an optical path length of the reference light LR. The reference light LR guided to the reference optical path length changing unit 94 is collimated into a parallel light flux by the collimator lens 95 and is guided to a corner cube 96. The corner cube 96 changes the traveling direction of the reference light LR that has been made into the parallel light flux by the collimator lens 95 in the opposite direction. The optical path of the reference light LR incident on the corner cube 96 and the optical path of the reference light LR emitted from the corner cube 96 are parallel. Further, the corner cube 96 is movable in a direction along the incident light path and the emitting light path of the reference light LR. Through this movement, the length of the optical path of the reference light LR is changed. The reference light LR emitted from the corner cube 96 is converted from the parallel light flux to the convergent light flux by a collimator lens 97 and enters an optical fiber f5, and is guided to a fiber coupler 93. A delay member or a dispersion compensation member may be provided between the collimator lens 95 and the corner cube 96 or between the corner cube 96 and the collimator lens 97. The delay member is an optical member for matching the optical path length (optical distance) of the reference light LR with the optical path length of the measurement light LS. The dispersion compensation member is an optical member for matching the dispersion characteristics between the reference light LR and the measurement light LS.

The measurement light LS which has been made into the parallel light flux by the collimator lens 86 is deflected one-dimensionally or two-dimensionally by an optical scanner 84. The optical scanner 84 includes a galvano mirror 84X and a galvano mirror 84Y. The galvano mirror 84X deflects the measurement light LS so as to scan the fundus Ef in the X direction. The galvano mirror 84Y deflects the measurement light LS deflected by the galvano mirror 84X so as to scan the fundus Ef in the Y direction. Examples of scan modes with the measurement light LS performed by the optical scanner 84 like this include horizontal scan, vertical scan, cross scan, radial scan, circle scan, concentric scan, helical (spiral) scan, and the like.

The measurement light LS deflected by the optical scanner 84 is reflected by the dichroic mirror 81 via a reflective mirror 83 and the focusing lens 82. The measurement light LS reflected by the dichroic mirror 81 is guided to the dichroic mirror 52 through the visual target projection system 4 and is reflected by the dichroic mirror 52. The light reflected by the dichroic mirror 52 is projected onto the subject's eye E through the objective lens 51. The measurement light LS is scattered (and reflected) at various depth positions of the subject's eye E. The returning light of the measurement light LS including such backscattered light advances through the same path as the outward path in the opposite direction and is guided to the fiber coupler 92, and then reaches the fiber coupler 93 through an optical fiber f3.

The fiber coupler 93 generates an interference light by superposing the measurement light LS incident through the optical fiber f3 and the reference light LR incident through the optical fiber f5 with each other (i.e., by making the measurement light LS incident through the optical fiber f3 and the reference light LR incident through the optical fiber f5 interfere with each other). The fiber coupler 93 generates a pair of interference light LC by splitting the interference light generated from the measurement light LS and the reference light LR at a predetermined splitting ratio (for example, 1:1). The pair of interference light LC emitted from the fiber coupler 93 is guided to the detector 98 through the optical fibers f6 and f7, respectively.

The detector 98 is, for example, a balanced photodiode (BPD) that includes a pair of photodetectors for respectively detecting the pair of the interference light LC and outputs the difference between the pair of detection results obtained by the pair of photodetectors. The difference of the detection results output from the detector 98 is sampled based on a clock generated in synchronization with the output timing of each wavelength sweeping (i.e., scanning) within a predetermined wavelength range by the OCT light source 91. This sampling data is sent to an arithmetic processing unit 120 in the processing unit 9. For example, the arithmetic processing unit 120 performs the Fourier transform, etc. on the spectral distribution based on the sampling data for each series of wavelength scanning (i.e., for each A line). With this, the reflection intensity profile for each A line is formed. In addition, the arithmetic processing unit 120 forms image data by applying imaging processing to the reflection intensity profiles of the respective A lines.

As described above, the OCT optical system 8 includes an interference optical system that splits light LO emitted from the OCT light source 91 into the reference light LR and the measurement light LS, irradiates the measurement light LS onto the subject's eye E, generates the interference light LC generated from the returning light of the measurement light LS and the reference light LR, and detects the generated interference light LC. This interference optical system irradiates the measurement light LS onto the subject's eye E via the objective lens 51 and the VCC lens 46.

The OCT optical system 8 like this is coupled to the optical path of the visual target projection system 4 by the dichroic mirror 81. In the case of coupling the optical path of the OCT optical system 8 with an optical path of another optical system using a perforated prism for example, it is necessary to consider vignetting of the measurement light or the returning light thereof and the like, since the optical system is configured to allow the measurement light to pass through the hole part of the perforated prism. Alternatively, in the case of coupling the OCT optical system 8 to another optical system (the refractometry projection system 6 and the refractometry light reception system 7) in which light having a wavelength close to the wavelength of the measurement light is used, since the wavelengths are close to each other, it becomes difficult to separate wavelengths and the efficiency is lowered. On the other hand, the optical path of the OCT optical system 8 is coupled to another optical system using the dichroic mirror 81, thereby the configuration of the optical system can be simplified and the degree of freedom of design of the optical system can be improved.

In addition, it becomes easier to add other optical systems and a configuration with expandability can be provided.

Moreover, the above two optical systems are coupled with each other at the side of the light source (upstream side) with respect to the VCC lens 46, thereby the measurement light LS is projected onto the fundus Ef through the VCC lens 46 and it is more likely to be converged to one point at the measurement site. Thus, with an optimum lateral resolution, an interference signal based on the detection results of the interference light can be acquired with sufficient intensity.

As shown in FIG. 3, an intermediate position between the VCC lens 46 and the pupil lens 45 is located in a position (pupil conjugate position Q) optically conjugate with a pupil of the subject's eye E. Similarly, an intermediate position between the galvano mirror 84X and the galvano mirror 84Y is located in a position optically conjugate with the pupil of the subject's eye E. Further, the focusing lens 82 is moved in the direction of the optical axis thereof so that the fundus Ef of the subject's eye E and the fiber end face of the optical fiber f2 are located in positions (fundus conjugate position P) optically conjugate with each other. The optical path of the OCT optical system 8 and the optical path of the visual target projection system 4 are coupled with each other at the side of the light source with respect to the pupil lens 45, thereby it becomes possible to make the fundus conjugate position P closer, and it is possible to downsize the visual target projection system 4 and the OCT optical system 8.

(Configuration of Processing System)

Figure 4:
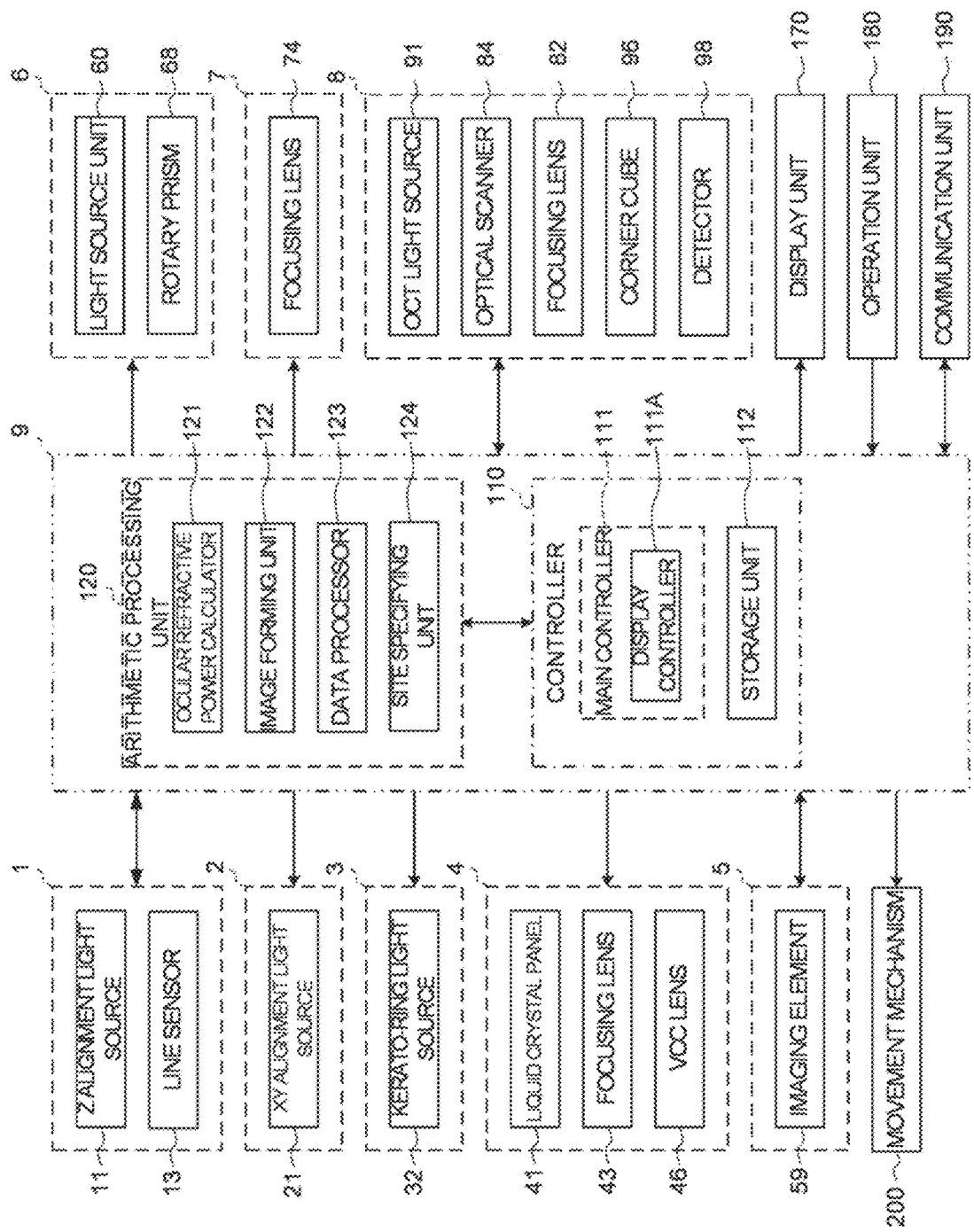
FIG. 4 is a schematic diagram illustrating an example of a configuration of a processing system of the ophthalmological device according to the embodiments.

A processing system of the ophthalmological device according to the embodiments is explained. FIG. 4 illustrates an example of the functional structure of the processing system of the ophthalmological device. FIG. 4 illustrates an example of a functional block diagram of the processing system of the ophthalmological device according to the embodiments. The processing unit 9 includes a controller 110 and the arithmetic processing unit 120. Further, the ophthalmological device according to the embodiments includes a display unit 170, an operation unit 180, a communication unit 190, and a movement mechanism 200.

The movement mechanism 200 is a mechanism for moving the head unit in front, back, left and right directions, the head unit housing the optical systems such as the Z alignment system 1, the XY alignment system 2, the keratometry system 3, the visual target projection system 4, the refractometry projection system 6, the refractometry light reception system 7, the OCT optical system 8, and the like. For example, the movement mechanism 200 is provided with an actuator that generates a driving force for moving the movement mechanism 200 and a transmission mechanism that transmits the driving force from the actuator to the movement mechanism 200. The actuator may be a pulse motor. The transmission mechanism may include a combination of gears, and a rack and pinion. The controller 110 (main controller 111) controls the movement mechanism 200 by sending a control signal to the actuator.

(Controller 110)

The controller 110 includes a processor and controls each part of the ophthalmological device. The controller 110 includes the main controller 111 and a storage unit 112. The storage unit 112 stores, in advance, a computer program for controlling the ophthalmological device. The computer program includes light source control programs, detector control programs, optical scanner control programs, optical system control programs, arithmetic processing programs, programs for user interface, and the like. The main controller 111 operates according to the computer programs, and thereby the controller 110 performs the control process.

The main controller 111 performs various controls of the ophthalmological device, as a measurement controller. Examples of control of the Z alignment system 1 include control of the Z alignment light source 11, control of the line sensor 13, and the like. Examples of the control of the Z alignment light source 11 include turning on and off of the light source, adjustment of amount of light, adjustment of aperture, and the like. Examples of the control of the line sensor 13 include adjustment of exposure of a detecting element, adjustment of gain of a detecting element, adjustment of detecting rate of a detecting element, and the like. Thereby, the Z alignment light source 11 can be switched between lighting and non-lighting or light amount can be changed. The main controller 111 acquires a signal detected by the line sensor 13 and specifies the projection position of light onto the line sensor 13 based on the acquired signal. The main controller 111 specifies a position of an apex of a cornea of the subject's eye E based on the specified projection position and controls the movement mechanism 200 based on the specified position to move the head unit in front and back directions (Z alignment).

Examples of control of the XY alignment system 2 include control of the XY alignment light source 21, and the like. Examples of the control of the XY alignment light source 21 include turning on and off of the light source, adjustment of amount of light, adjustment of aperture, and the like. Thereby, the XY alignment light source 21 can be switched between lighting and non-lighting, or light amount can be changed. The main controller 111 acquires a signal detected by the imaging element 59, and specifies a position of a bright spot image on the basis of returning light of the light from the XY alignment light source 21 based on the acquired signal. The main controller 111 controls the movement mechanism 200 to move the head unit in left and right directions so as to cancel a displacement the position of the bright spot image with respect to a predetermined target position (for example, a center position of the alignment mark) (XY alignment).

Examples of control of the keratometry system 3 include control of the kerato-ring light source 32, and the like. Examples of the control of the kerato-ring light source 32 include turning on and off of the light source, adjustment of amount of light, adjustment of aperture, and the like. Thereby, the kerato-ring light source 32 can be switched between lighting and non-lighting, or light amount can be changed. The main controller 111 controls the arithmetic processing unit 120 to perform a known calculation on a kerato-ring image detected by the imaging element 59. Thereby, corneal shape parameters of the subject's eye E are obtained.

Examples of control of the visual target projection system 4 include control of the liquid crystal panel 41, control of the focusing lens 43, control of the VCC lens 46, and the like. Examples of the control of the liquid crystal panel 41 include displaying on and off of the visual targets and the fixation target, switching the display position of the fixation target, and the like. Thereby, the visual target or the fixation target is projected onto the fundus Ef of the subject's eye E. Examples of the control of the focusing lens 43 include control of moving the focusing lens 43 in the optical axis direction, and the like. For example, the visual target projection system 4 includes a movement mechanism that moves the focusing lens 43 in the optical axis direction. As is the case with the movement mechanism 200, this movement mechanism is provided with an actuator that generates a driving force for moving this movement mechanism and a transmission mechanism that transmits the driving force from the actuator to this movement mechanism. The main controller 111 controls the movement mechanism by sending a control signal to the actuator to move the focusing lens 43 in the optical axis direction. Thereby, the position of the focusing lens 43 is adjusted so that the liquid crystal panel 41 and the fundus Ef are optically conjugate with each other. Examples of the control of the VCC lens 46 include control of changing astigmatic power and astigmatic axis angle, and the like. The VCC lens 46 includes a pair of concave and convex cylinder lenses which are relatively rotatable around their optical axes. The main controller 111 controls the pair of cylinder lenses to rotate relatively so as to correct the astigmatic state (the astigmatic power and the astigmatic axis angle) of the subject's eye E obtained separately by the refractometry described after, for example.

Examples of control of the observation system 5 include control of the imaging element 59, and the like. Example of the control of the imaging element 59 include adjustment of exposure of the imaging element 59, adjustment of gain of the imaging element 59, adjustment of detecting rate of the imaging element 59, and the like. The main controller 111 acquires a signal detected by the imaging element 59 and controls the arithmetic processing unit 120 to perform processing such as forming image based on the acquired signal and the like. Note that, in case that the observation system 5 include an illumination light source, the main controller 111 is capable of controlling the illumination light source.

Examples of control of the refractometry projection system 6 include control of the light source unit 60, control of the rotary prism 68, and the like. Examples of the control of the light source unit 60 include control of the refractometry light source 61, control of the light source unit 60, and the like. Examples of the control of the refractometry light source 61 include turning on and off of the light source, adjustment of amount of light, adjustment of aperture, and the like. Thereby, the refractometry light source 61 can be switched between lighting and non-lighting, or light amount can be changed. Examples of the light source unit 60 include control of moving the light source unit 60 in the optical axis direction. For example, the refractometry projection system 6 include a movement mechanism that moves the light source unit 60 in the optical axis direction. As is the case with the movement mechanism 200, this movement mechanism is provided with an actuator that generates a driving force for moving this movement mechanism and a transmission mechanism that transmits the driving force from the actuator to this movement mechanism. The main controller 111 controls the movement mechanism by sending a control signal to the actuator to move the light source unit 60 in the optical axis direction. Examples of the control of the rotary prism 68 include control of rotating the rotary prism 68 and the like. For example, a rotary mechanism that rotates the rotary prism 68 is provided and the main controller 111 controls the rotary mechanism to rotate the rotary prism 68.

Examples of control of refractometry light reception system 7 include control of the focusing lens 74, and the like. Examples of the control of the focusing lens 74 include control of moving the focusing lens 74 in the optical axis direction. For example, the refractometry light reception system 7 include a movement mechanism that moves the focusing lens 74 in the optical axis direction. As is the case with the movement mechanism 200, this movement mechanism is provided with an actuator that generates a driving force for moving this movement mechanism and a transmission mechanism that transmits the driving force from the actuator to this movement mechanism. The main controller 111 controls the movement mechanism by sending a control signal to the actuator to move the focusing lens 74 in the optical axis direction. The main controller 111 is capable of moving the light source unit 60 and the focusing lens 74 respectively depending on the refractive power of the subject's eye E for example so that the refractometry light source 61 and the imaging element 59 are optically conjugate with each other.

Examples of control of the OCT optical system 8 include control of the OCT light source 91, control of the optical scanner 84, control of the focusing lens 82, control of the corner cube 96, control of the detector 98, and the like. Examples of the control of the OCT light source 91 include turning on and off of the light source, adjustment of amount of light, adjustment of aperture, and the like. Examples of the control of the optical scanner 84 include control of the scanning position and the scanning area and the scanning speed by means of the galvano mirror 84X, control of the scanning position and the scanning area and the scanning speed by means of the galvano mirror 84Y, and the like. Examples of the control of the focusing lens 82 include control of moving the focusing lens 82 in the optical axis direction, and the like. For example, the OCT optical system 8 include a movement mechanism that moves the focusing lens 82 in the optical axis direction. As is the case with the movement mechanism 200, this movement mechanism is provided with an actuator that generates a driving force for moving this movement mechanism and a transmission mechanism that transmits the driving force from the actuator to this movement mechanism. The main controller 111 controls the movement mechanism by sending a control signal to the actuator to move the focusing lens 82 in the optical axis direction. For example, the main controller 111 may moves the focusing lens 82 alone based on the intensity of the interference signal, after moving the focusing lens 82 in conjunction with the movement of the focusing lens 43. Examples of the control of the corner cube 96 include control of moving the corner cube 96 in the optical axis direction. For example, the OCT optical system 8 include a movement mechanism that moves the corner cube 96 in the optical axis direction. As is the case with the movement mechanism 200, this movement mechanism is provided with an actuator that generates a driving force for moving this movement mechanism and a transmission mechanism that transmits the driving force from the actuator to this movement mechanism. The main controller 111 controls the movement mechanism by sending a control signal to the actuator to move the corner cube 96 in the optical axis direction. Thereby, the length of the optical path of the reference light LR is changed. Examples of the control of the detector 98 include adjustment of exposure of a detecting element, adjustment of gain of a detecting element, adjustment of detecting rate of a detecting element, and the like. The main controller 111 performs sampling of the signal detected by the detector 98 and controls the arithmetic processing unit 120 (an image forming unit 122) to perform processing such as forming image based on the sampled signal and the like.

The main controller 111 includes the display controller 111A. The display controller 111A displays various kinds of information on a display unit 170. Examples of the information displayed on the display unit 170 include a result of the objective measurement and a result of the subjective inspection acquired by using the above optical system, an image (a tomographic image, etc.) based on the image data formed by the image forming unit 122, an image and information on which the image processing or the data processing is performed by the data processor 123, and the like. The display controller 111A can superimpose these kinds of information and display them on display unit 170, or can identify and display a part of the information.

Further, the main controller 111 performs a process of writing data in the storage unit 112 and a process of retrieving data from the storage unit 112.

(Storage Unit 112)

The storage unit 112 stores various kinds of data. Examples of the data stored in the storage unit 112 include an inspection result of the subjective inspection, a measurement result of the objective measurement, image data of a tomographic image, image data of a fundus image, subject's eye information, and the like. The subject's eye information includes information on the subject such as patient ID and name, and information on the subject's eye such as identification information of the left eye/right eye. The storage unit 112 further stores various types of programs and data to run the ophthalmological device.

(Arithmetic Processing Unit 120)

The arithmetic processing unit 120 include an ocular refractive power calculator 121, the image forming unit 122, a data processor 123, and a site specifying unit 124.

The ocular refractive power calculator 121 analyzes a ring image (pattern image) acquired by receiving the returning light of the ring-shaped light flux (ring-shaped measurement pattern) projected onto the fundus Ef by the refractometry projection system 6 by the imaging element 59. For example, the ocular refractive power calculator 121 obtains a position of the center of gravity of the ring image from the brightness distribution in the image representing the acquired ring image, obtains brightness distributions along a plurality of scanning directions extending radially from the position of the center of gravity, and specifies a ring image from this brightness distributions. Subsequently, the ocular refractive power calculator 121 obtains an approximate ellipse of the specified ring image and obtains a spherical power S, an astigmatic power C, and an astigmatic axis angle A by assigning a major axis and a minor axis of the approximate ellipse to a known formula.

The ocular refractive power calculator 121 is capable of specifying the ring image from new data group acquired by deleting part of data group used for specifying the above ring image. Further, the ocular refractive power calculator 121 may specify the ring image from new data group acquired by replacing a part of data group used for specifying the above ring image with interpolation data. In this case, the interpolation data is obtained by an interpolation processing using data other than the part of data group. The ocular refractive power calculator 121 obtains an approximate ellipse of the specified new ring image and obtains a new spherical power S, a new astigmatic power C, and a new astigmatic axis angle A from the approximate ellipse. The deleted or interpolated "part of data group" is data acquired from a measurement result (for example, brightness distributions) of the site specified by the site specifying unit 124 described after or data designated by the user. Thereby, the measurement result, which may be lowered the accuracy of the spherical power S and the like, obtained by the ocular refractive power measurement can be deleted or interpolated from the measurement result (for example, the brightness distributions in the predetermined scanning direction). Thus, it is possible to suppress deterioration of the accuracy of the spherical power S and the like obtained by the ocular refractive power measurement.

Alternatively, the ocular refractive power calculator 121 can obtain the ocular refractive power parameter based on deformation and displacement of the ring image with respect to the reference pattern. In this case, the ocular refractive power calculator 121 specifies deformation and displacement of a new ring image by deleting or interpolating a part of the deformation and the displacement of the ring image with respect to the reference pattern as above, and obtains the ocular refractive power parameter based on the deformation and the displacement of the specified ring image.

Further, the ocular refractive power calculator 121 calculates a corneal refractive power, a corneal astigmatism power, and a corneal astigmatic axis angle based on the kerato-ring image acquired by the observation system 5. For example, the ocular refractive power calculator 121 calculates a corneal curvature radius of the steepest meridian and/or the flattest meridian of the anterior surface of the cornea by analyzing the kerato-ring image and calculates above parameters based on the corneal curvature radius.

The image forming unit 122 forms image data of a tomographic image of the fundus Ef based on a signal detected by the detector 98. That is, the image forming unit 122 forms the image data of the subject's eye E based on a detection result of the interference light LC obtained by the interference optical system. As in the conventional swept-source-type OCT, the image formation processing includes filtering, fast Fourier transform (FFT), and the like. The image data acquired in this manner is a data set including a group of image data formed by imaging the reflection intensity profiles of a plurality of A lines. Here, the A lines are the paths of the measurement light LS in the subject's eye E.

In order to improve the image quality, it is possible to repeatedly perform scan with the same pattern a plurality of times to collect a plurality of data sets, and to compose (i.e., average) the plurality of data sets.

The data processor 123 performs various kinds of data processing (e.g., image processing) and various kinds of analysis on a tomographic image formed by the image forming unit 122. For example, the data processor 123 performs various correction processes such as brightness correction and dispersion correction of images. Further, the data processor 123 performs various types of image processing and analysis on images (anterior ocular segment image, etc.) acquired using the observation system 5.

The data processor 123 can form volume data (voxel data) of the subject's eye E by performing known image processing such as interpolation processing for interpolating pixels between tomographic images. In the case of displaying an image based on the volume data, the data processor 123 performs rendering process on the volume data so as to form a pseudo three-dimensional image viewed from a specific line-of-sight direction.

The data processor 123 is capable of performing segmentation processing for specifying a plurality of partial data sets corresponding to a plurality of tissues of the subject's eye, by analyzing the three-dimensional data set formed by the image forming unit 122, for example. The segmentation processing is image processing for determining specific tissues and/or tissue boundaries. For example, the data processor 123 determines the gradients of the pixel values (i.e., brightness values) in each A mode image included in the three-dimensional data set, and specifies a position where the gradient value is large to be a tissue boundary. Note that the A mode image is one-dimensional image data extending in the depth direction (Z direction) of the fundus.

In the present embodiments, the data processor 123 specifies a plurality of partial data sets corresponding to a plurality of layer tissues of the fundus by analyzing the three-dimensional data set representing the fundus (the retina, the choroid, etc.) and the vitreous body. Each partial data set is defined by the boundaries of a layer tissue. Examples of the layer tissue specified as a partial data set include layer tissues of the retina such as the inner limiting membrane, the nerve fiber layer, the ganglion cell layer, the inner plexiform layer, the inner nuclear layer, the outer plexiform layer, the outer nuclear layer, the external limiting membrane, the photoreceptor layer, the retinal pigment epithelium layer. As another example, it is possible to specify a partial data set corresponding to the Bruch membrane, the choroid, the sclera, the vitreous body, or the like. Further, it is also possible to specify a partial data set corresponding to a lesion part. Examples of lesion parts include a detachment part, an edema, a bleeding site, a tumor, a drusen, and the like.

The site specifying unit 124 specifies an attention site of the subject's eye based on the returning light from the subject's eye E detected by using the refractometry light reception system 7. Examples of the attention site include a diseased site, a designated site having a form designated by the user, and the like. For example, the site specifying unit 124 specifies the diseased site according to distortion or deformation of the ring image specified by the ocular refractive power calculator 121. The site specifying unit 124 obtains a residual error (displacement amount) from the approximate ellipse in the ring image specified by the ocular refractive power calculator 121, and detects the residual error(s) equal to or greater than a predetermined threshold value among the obtained residual errors as the outlier(s). The site specifying unit 124 specifies a part (or region included this part) where the outlier is detected, as the diseased site. Further, the site specifying unit 124 is capable of specifying, as the diseased site, a part where the amount of reflected light has decreased from the ring image specified by the ocular refractive power calculator 121. In this case, the site specifying unit 124 refers to the image formed by the image forming unit 122 and specifies, as the diseased site, a region including a part where the brightness change of the site projected by refractometry projection system 6 is equal to or greater than a predetermined threshold value. Further, the site specifying unit 124 may specify the diseased site base on the light amount distribution of the specified ring image (for example, the light amount distribution on the straight line passing through the center part of the ring image) or the deviation of the specified ring image. For example, the site specifying unit 124 specifies the diseased site base on the contrast of the ring image. In this case, it is possible to specify, as the diseased site, a part where the difference between the maximum value and the minimum value of the light amount distribution of the ring image is equal to or less than a predetermined threshold value. The subject's eye with low contrast like this has suspicion of a cataract eye, and can be a target of an OCT imaging. Alternatively, for example, the site specifying unit 124 is capable of specifying, as the designated site, a part deviated from the approximate ellipse with the form designated by the user in the ring image specified by the ocular refractive power calculator 121. Further, the site specifying unit 124 is capable of specifying the diseased site base on the detection result of the interference light by the OCT optical system 8. For example, the site specifying unit 124 compares the plurality of the layer tissues of the fundus Ef, which are detected by the segmentation processing performed on the tomographic image formed based on the detection result of the interference light by the OCT optical system 8, with standard values (standard thicknesses) of the plurality of the layer tissues of the fundus of healthy eyes and specifies, as the diseased site or an abnormal site, a part where the difference is equal to or greater than a predetermined threshold value.

(Display Unit 170, Operation Unit 180)

Upon receiving control of the controller 110, the display unit 170 displays information, as an interface unit. The display unit 170 includes the display unit 10 shown in FIG. 1 and the like.

The operation unit 180 is used to operate the ophthalmological device, as the interface unit. The operation unit 180 includes various types of hardware keys (the joystick, buttons, switches, etc.) provided in the ophthalmological device. Further, the operation unit 180 may include various kinds of software keys (buttons, icons, menus, etc.) displayed on the touch panel type display screen 10a.

At least part of the display unit 170 and of the operation unit 180 may be integrally configured. A typical example of this is the touch-panel display screen 10a.

(Communication Unit 190)

The communication unit 190 has the function of communicating with an external device (not shown). The communication unit 190 may be provided in the processing unit 9, for example. The communication unit 190 has a structure corresponding to the mode of communication with the external device.

The visual target projection system 4 is an example of the "subjective inspection optical system" according to the embodiments. The OCT optical system 8 is an example of the "interference optical system" according to the embodiments. The refractometry projection system 6, the refractometry light reception system 7, and part of the observation system 5 (the half mirror 76, the imaging lens 58, and the imaging element 59) are an example of the "objective measurement optical system" according to the embodiments. The site specifying unit 124 is an example of the "attention site specifying unit" according to the embodiments.

<Operation Example>

Described below is an example of the operation of the ophthalmological device of the embodiments.

Figure 5:
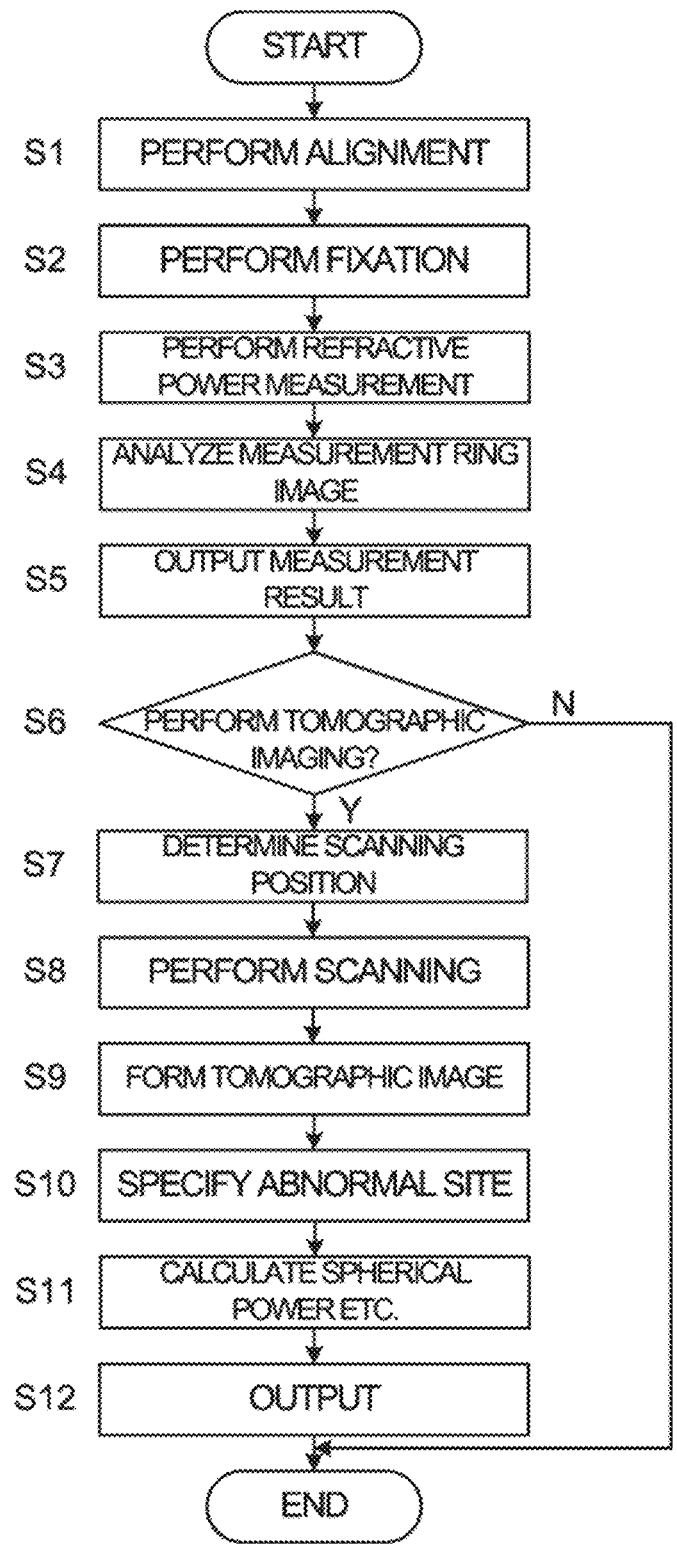
FIG. 5 is a flowchart illustrating an example of an operation of the ophthalmological device according to the embodiments.
Figure 6A:
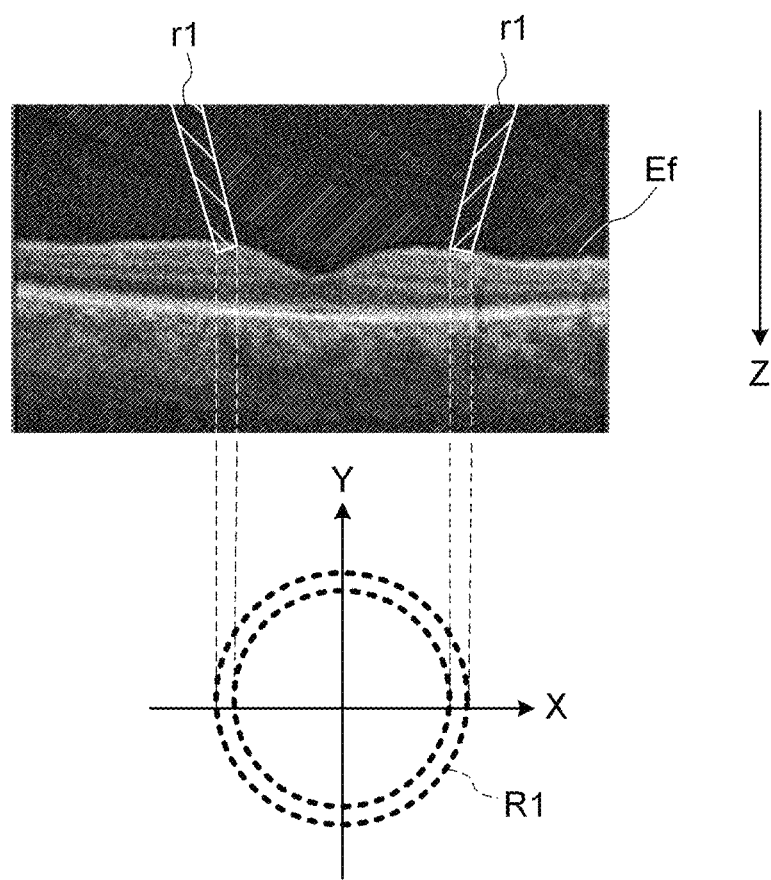
FIG. 6A is an explanatory diagram of the operation of the ophthalmological device according to the embodiments.
Figure 6B:
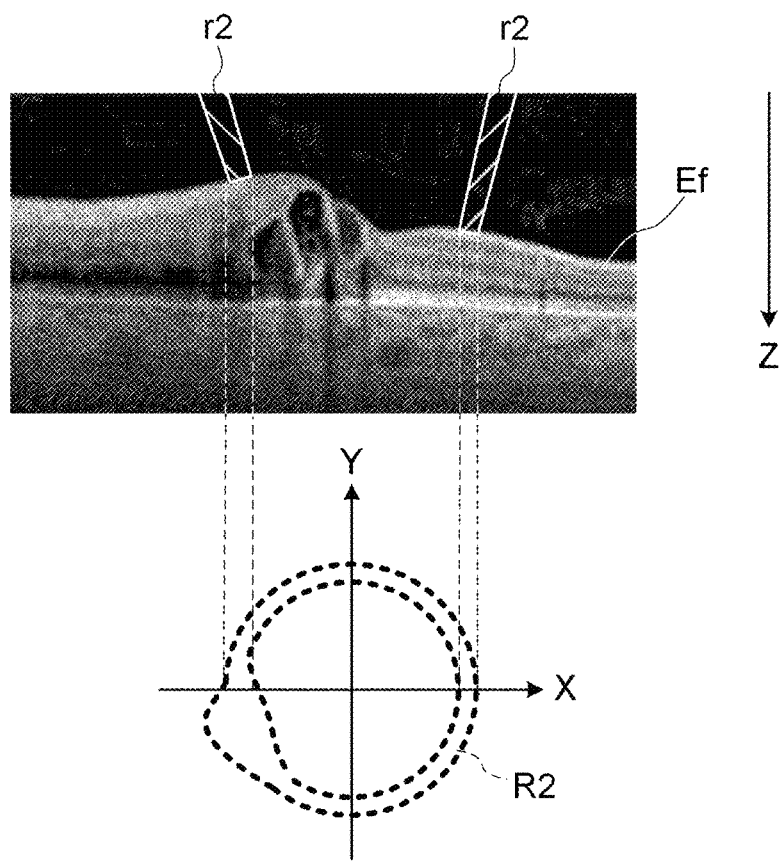
FIG. 6B is an explanatory diagram of the operation of the ophthalmological device according to the embodiments.

FIG. 5 shows a flow chart of an operation example of the ophthalmological device according to the embodiments. FIGS. 6A, 6B, and 7 to 10 are explanatory diagrams of the operation of the ophthalmological device according to the embodiments.

(S1)

After the face of the subject is fixed by the face support unit, the head unit is moved to an inspection position for the subject's eye E by the XY alignment performed by using the XY alignment system 2 and the Z alignment performed by using the Z alignment system 1. The inspection position is a position where the inspection of the subject's eye E can be performed. For example, the processing unit 9 (controller 110) acquires imaging signal of an anterior ocular segment image formed on the imaging surface of the imaging element 59 and controls the display unit 170 to display the anterior ocular segment image E' (on display screen 10a of the display unit 10). After that, the head unit is moved to at the inspection position of the subject's eye E by performing the above XY alignment and Z alignment. The movement of the head unit is executed by the controller 110 in accordance with an instruction from the controller 110, but may be executed by the controller 110 in accordance with an operation or an instruction by the user.

Further, the controller 110 moves the refractometry light source 61, the focusing lens 74, and the focusing lens 43 in conjunction with each other along the optical axis to a position corresponding to an origin (for example, 0 D).
(S2)

The controller 110 controls the liquid crystal panel 41 to display the fixation target. Thereby, the subject's eye E is gazed at the desired fixation position.
(S3)

Next, the controller 110 performs the objective measurement. That is, the controller 110 controls the refractometry projection system 6 to project the ring-shaped light flux onto the fundus Ef of the subject's eye E, and controls the refractometry light reception system 7 to detect the returning light by the imaging element.
(S4)

Next, the controller 110 controls the ocular refractive power calculator 121 to analyze the ring image based on the returning light detected in S3. The ocular refractive power calculator 121 specifies the ring image described above, obtains an approximate ellipse of the specified ring image, and obtains a spherical power S, an astigmatic power C, and an astigmatic axis angle A by assigning a major axis and a minor axis of the approximate ellipse to a known formula. In the controller 110, the calculated spherical power S and the like are stored in the storage unit 112.

In the case that the subject's eye E is a healthy eye (FIG. 6A), when the ring-shaped light flux r1 is projected onto the fundus Ef, the shape of the ring image R1 based on the returning light thereof has a shape with almost no residual errors from the approximate ellipse. On the other hand, in the case that the subject's eye E is a diseased eye which has an edema (the diseased site) on the fundus Ef (FIG. 6B), when the ring-shaped light flux r2 is projected onto the fundus Ef, the shape of the ring image R2 based on the returning light from the fundus Ef has a shape with a large residual error the approximate ellipse in the vicinity of the diseased site. Thus, the site specifying unit 124 obtains the residual error(s) (displacement amount) from the approximate ellipse in the ring image based on the returning light detected in S3 as described above, and detects, as the outlier(s), the residual error(s) equal to or greater than the predetermined threshold value among the obtained residual errors. The site specifying unit 124 specifies, as the diseased site, the part where the outlier(s) is/are detected.

Figure 7:
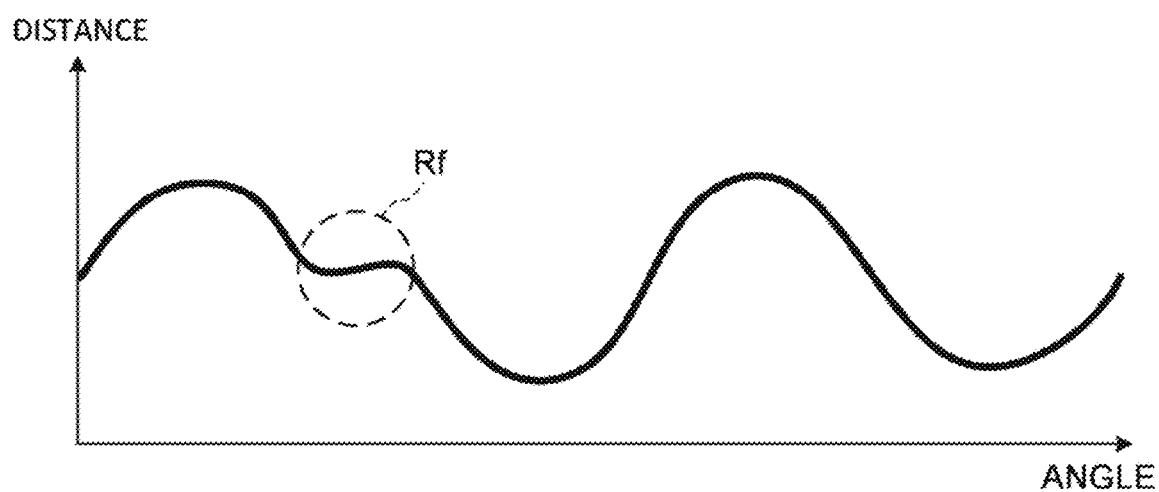
FIG. 7 is an explanatory diagram of the operation of the ophthalmological device according to the embodiments.
Figure 8:
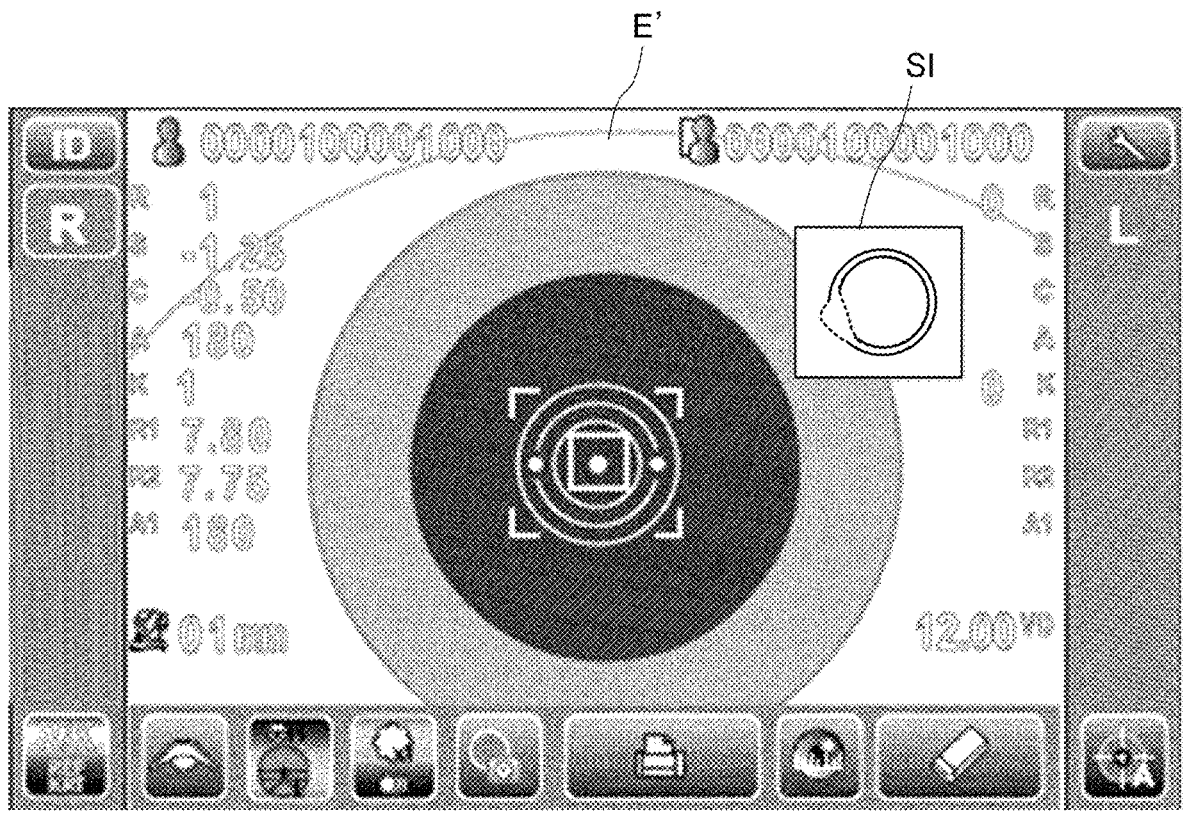
FIG. 8 is an explanatory diagram of the operation of the ophthalmological device according to the embodiments.

FIG. 7 illustrates an example of the shape of the ring image based on the returning light of the ring-shaped light flux projected onto the fundus Ef of the diseased eye. In FIG. 7, with a reference line in the predetermined direction as a reference, the horizontal axis represents the angle between the reference line and the straight line connecting the center of gravity position and the sampling point of the ring image, and the vertical axis represents the distance from the center of gravity position to the sampling point of the ring image. In FIG. 7, the part Rf having large residual error(s) is specified as the diseased site.

In addition, the controller 110 is capable of performing keratometry before or after the refractometry. In this case, the controller 110 controls the kerato-ring light source 32 to turn on and controls the ocular refractive power calculator 121 to analyze the kerato-ring image detected by the imaging element 59. The ocular refractive power calculator 121 obtains the corneal curvature radius by analyzing the kerato-ring image as above, and calculates the corneal refractive power, the corneal astigmatism power, and the corneal astigmatic axis angle from the obtained the corneal curvature radius. In the controller 110, the calculated corneal refractive power and the like are stored in the storage unit 112.
(S5)

The display controller 111A displays the result of the objective measurement acquired in S4 on the display unit 170. Examples of the result of the objective measurement displayed on the display unit 170 include the spherical power S, the astigmatic power C, the astigmatic axis angle A, the corneal refractive power, the corneal astigmatism power, the corneal astigmatic axis angle, and the like.

Further, the display controller 111A may display the information SI representing the diseased site specified in S4 along with the anterior ocular segment image E' of the subject's eye E. For example, the display controller 111A displays the diseased site specified by the site specifying unit 124 in S4 so as to identify the site. The mode of displaying the diseased site so as to identify it includes highlighting and the like. Examples of highlighting of the diseased site include blinking display of the diseased site, color-coded display which makes the color of the diseased site different from the color of the other site, both of them, and the like. Further, only when the diseased site is specified by the site specifying unit 124 in S4, the display controller 111A may display the information representing the diseased site on the display unit 170. Alternatively, the display controller 111A may display the information representing the specified ring image or the specified diseased site by performing a touch operation on the ring-shaped light flux projection part depicted together with the anterior ocular segment image E'.
(S6)

Next, the controller 110 determines whether or not to perform tomographic imaging. For example, the controller 111 determines whether or not to perform tomographic imaging based on the operation with respect to the operation unit 180 by the user who has referred to the information displayed on the display unit 170 in S5. When it is determined that tomographic imaging is to be performed (S6: Y), the operation of the ophthalmological device moves to S7. When it is determined that tomographic imaging is not to be performed (S6: N), the ophthalmological device terminates the operation (end).

Further, the controller 110 is capable of controlling the ophthalmological device to perform tomographic image automatically based on the result of the objective measurement acquired in S4. For example, in case that the diseased site is specified by the site specifying unit 124, the controller 110 may control the ophthalmological device to perform tomographic imaging automatically.
(S7)

Figure 9:
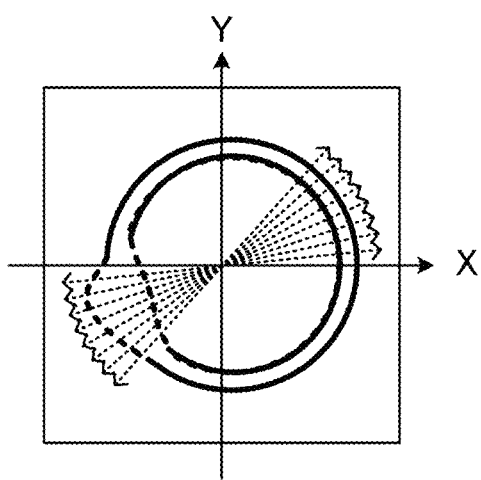
FIG. 9 is an explanatory diagram of the operation of the ophthalmological device according to the embodiments.

When it is determined in S6 that the tomographic imaging is to be performed (S6: Y), the controller 110 obtains the scanning position(s) and the scanning direction(s) for projecting the measurement light onto the subject's eye E so as to overlap at least part of the irradiated area of the ring-shaped light flux on the fundus Ef irradiated by the refractometry projection system 6. In the present embodiments, as shown in FIG. 9, the controller 110 obtains the scanning position(s) and the scanning direction(s) by a plurality of radial scans so as to traverse the vicinity of the diseased site specified in S4.

Note that, the controller 110 may obtain the scanning position(s) for scanning with one or more circle scans so as to traverse the vicinity of the diseased site specified in S4. The diameter of the circle scan can be the diameter of the ring passing through the center of the width of the ring-shaped light flux projected onto the fundus Ef by the refractometry projection system 6.

(S8)

The controller 110 controls the optical scanner 84 to scan the fundus Ef with the measurement light LS using the scanning position(s) and the scanning direction(s) obtained in S7.

(S9)

The controller 110 controls the arithmetic processing unit 120 to form a tomographic image of the diseased site based on the detection result of the interference light acquired by the scan in S8. In the present embodiments, since the scan is performed on the specified diseased site, the scan time can be greatly shortened. In addition, since the OCT optical system 8 is coaxial with the refractometry projection system 6, the center of the ring-shaped light flux always coincides with the center of the scan. Thereby, the diseased site on which the ring-shaped light flux is projected can be scanned accurately.

(S10)

Figure 10:
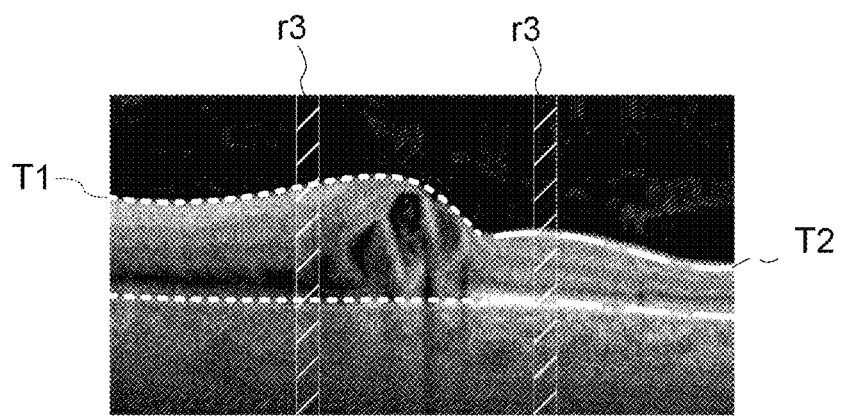
FIG. 10 is an explanatory diagram of the operation of the ophthalmological device according to the embodiments.

The data processor 123 performs the segmentation processing on the tomographic image by analyzing the data set formed in S9, and detects a plurality of the layer tissues at the fundus Ef. The storage unit 112 previously stores the standard values (standard thicknesses) of the plurality of the layer tissues of the fundus of healthy eyes, as the standard data (Normative Data). The site specifying unit 124 (or the data processor 123) compares the thicknesses of the plurality of the layer tissues detected by the segmentation processing with the standard data stored in the storage unit 112, and specifies the part having the difference equal to or greater than the predetermined threshold value as the abnormal site. As shown in FIG. 10, the display controller 111A displays the specified abnormal site so as to identify the site on the display unit 170 together with the tomographic image formed in S9. In FIG. 10, the situation, that the normal site T2 and the thickness abnormal site T1 as the abnormal site are specified, is represented for the fundus Ef onto which the ring-shaped light flux r3 is projected.

Note that, the user may specify the abnormal site of the subject's eye E by observing the tomographic image displayed on the display unit 170 and may designate the specified cite using the operation unit 180.

(S11)

The ocular refractive power calculator 121 specifies the new ring image by deleting or interpolating the data at the abnormal site specified in S10 from the data group for specifying the ring image acquired in S3. The ocular refractive power calculator 121 obtains the approximate ellipse of the newly specified ring image, and obtains a new spherical power S, a new astigmatic power C, and a new astigmatic axis angle A from the approximate ellipse.

(S12)

The display controller 111A displays the newly obtained spherical power S, the astigmatic power C, and the astigmatic axis angle A on the display unit 170 together with the tomographic image and the abnormal site in S11. This terminates the operation of the ophthalmological device (END).

Note that, when it is determined that tomographic imaging is not to be performed (S6: N), the controller 110 may perform the subjective inspection. In this case, the controller 110 controls the focusing lens 43 and the VCC lens 46 so as to correct the spherical power S, the astigmatic power C, and the astigmatic axis angle A obtained in S4. Next, the controller 110 controls the liquid crystal panel 41 to display the desired visual target based on the instruction by the user with respect to the operation unit 180, for example. The subject responses with respect to the visual target projected onto the fundus Ef. For example, in the case of the visual target for the visual acuity measurement, the visual acuity value of the subject's eye is determined based on the responses from the subject. Selection of the visual target and response of the subject with respect to the selected visual target are repeatedly performed on the basis of the determination of the examiner or of the controller 110. The examiner or the controller 110 determines the visual acuity values or the prescription values (S, C, A) based on the responses from the subject.

Examples of Modifications

The configuration of the ophthalmological device according to the embodiments is not limited to the configuration explained in FIGS. 1 and 2.

For example, in the optical scanner 84 in the OCT optical system 8, a reflective mirror and two relay lenses may be disposed between the galvano mirror 84Y and the galvano mirror 84X. The galvano mirror 84X is disposed at a focal position on the upstream side of one of the relay lenses. The galvano mirror 84Y is disposed at a focal position on the downstream side of the other relay lens 87A. The reflective mirror is disposed so as to guide the measurement light LS deflected by the galvano mirror 84X to the galvano mirror 84Y. The galvano mirror 84Y and the galvano mirror 84X are disposed at the positions (pupil conjugate position Q) optically conjugate with the pupil of the subject's eye E, respectively. In this case, since both the galvano mirror 84X and the galvano mirror 84Y are disposed at the pupil conjugate positions Q, the interference light can be detected with higher lateral resolution than in the embodiments. Further, since the galvano mirror 84X and the galvano mirror 84Y are disposed at optically conjugate positions, even when the focusing lens 82 is moved, the intensity of the interference light can be enhanced and the tomographic image with higher image quality can be obtained while keeping the conjugate relationship.

The ophthalmological device according to the embodiments or the modification examples thereof can be applied to an ophthalmological inspection system capable of performing inspection of both eyes.

<Ophthalmological Inspection System>

Figure 11:
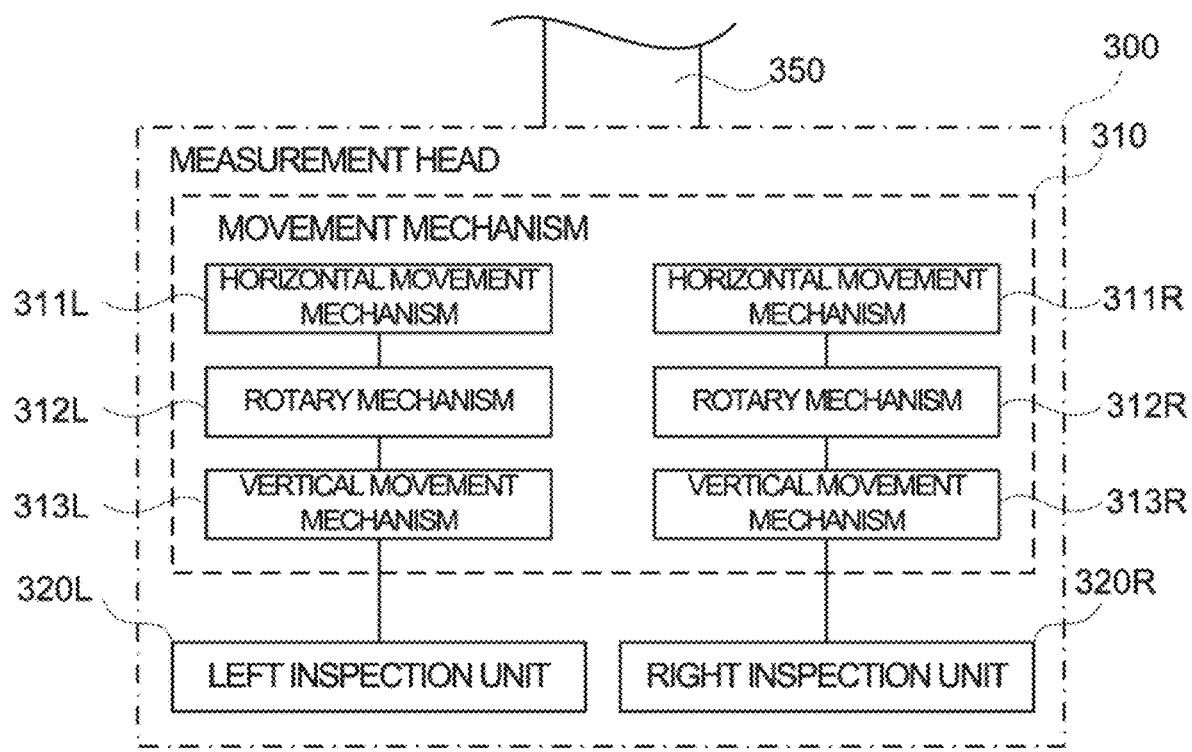
FIG. 11 is a schematic diagram illustrating an example of a configuration of an ophthalmological inspection system to which the ophthalmological device according to the embodiments is applied.

FIG. 11 is a block diagram of a configuration example of the ophthalmological inspection system to which the ophthalmological device according to the embodiments or the modification examples thereof is applied.

The ophthalmological inspection system includes a measurement head 300. The measurement head 300 is hanged from up above by a holding unit 350 supported by a supporting member (not shown). The measurement head 300 include a movement mechanism 310, a left inspection unit 320L, and a right inspection unit 320R. An optometry window (not shown) is formed in each of the left inspection unit 320L and the right inspection unit 320R. A left eye of the subject (left subject's eye) is inspected through an optometry window provided in the left inspection unit 320L. A right eye of the subject (right subject's eye) is inspected through an optometry window provided in the right inspection unit 320R.

The left inspection unit 320L and the right inspection unit 320R are moved three-dimensionally independently or in conjunction with each other. At least one of the left inspection unit 320L and the right inspection unit 320R is provided with the ophthalmological device according to the embodiments or the modification example thereof.

The movement mechanism 310 includes horizontal movement mechanisms 311L and 311R, rotary mechanisms 312L and 312R, and vertical movement mechanisms 313L and 313R.

The horizontal movement mechanism 311L moves the rotary mechanism 312L, the vertical movement mechanism 313L, and the left inspection unit 320L in a horizontal direction (lateral direction (X direction), front-back direction (Z direction)). Thereby, a position of the optometry window in the horizontal direction can be adjusted depending on an arranged position of the left subject's eye. For example, the horizontal movement mechanism 311L is provided with a known configuration using a drive means and a driving force transmission means that transmits driving force generated by the drive means, receives a control signal from a control device (not shown) and moves the rotary mechanism 312L, etc. in the horizontal direction. The horizontal movement mechanism 311L is capable of moving the rotary mechanism 312L, etc. in the horizontal direction manually under reception of the operation by an operator.

The horizontal movement mechanism 311R moves the rotary mechanism 312R, the vertical movement mechanism 313R, and the right inspection unit 320R in the horizontal direction. Thereby, a position of the optometry window in the horizontal direction can be adjusted depending on an arranged position of the right subject's eye. The horizontal movement mechanism 311R has the same configuration as the horizontal movement mechanism 311L, receives a control signal from a control device (not shown) and moves the rotary mechanism 312R, etc. in the horizontal direction. The horizontal movement mechanism 311R is capable of moving the rotary mechanism 312R, etc. in the horizontal direction manually under reception of the operation by the operator.

The rotary mechanism 312L rotates the vertical movement mechanism 313L and the left inspection unit 320L around a rotation axis (left rotation axis) for the left eye extending in the vertical direction (approximate vertical direction). The angle formed by this rotation axis and the horizontal plane can be changed. For example, the rotary mechanism 312L is provided with a known configuration using a drive means and a driving force transmission means that transmits driving force generated by the drive means, receives a control signal from a control device (not shown) and rotates the left inspection unit 320L, etc. around the rotate axis. The rotary mechanism 312L is capable of rotating the left inspection unit 320L, etc. around the rotation axis manually under reception of the operation by the operator.

The rotary mechanism 312R rotates the vertical movement mechanism 313R and the right inspection unit 320R around a rotation axis (right rotation axis) for the right eye extending in the vertical direction. The angle formed by this rotation axis and the horizontal plane can be changed. The rotation axis for the right eye is an axis arranged at a position separated from the rotation axis for the left eye by a predetermined distance. The distance between the rotation axis for the left eye and the rotation axis for the right eye can be adjusted. The rotary mechanism 312R has the same configuration as the rotary mechanism 312L, receives a control signal from a control device (not shown) and rotates the right inspection unit 320R, etc. around the rotate axis. The rotary mechanism 312R is capable of rotating the right inspection unit 320R, etc. around the rotation axis manually under reception of the operation by the operator.

The orientation of the left inspection unit 320L and the right inspection unit 320R can be changed relatively, by rotating the left inspection unit 320L and the right inspection unit 320R by the rotary mechanisms 312L and 312R. For example, the left inspection unit 320L and the right inspection unit 320R are respectively rotated in opposite directions around the eyeball rotation points of the left and right eyes of the subject. Thereby, the subject's eyes can be congested.

The vertical movement mechanism 313L moves the left inspection unit 320L in the up-down direction (vertical direction, Y direction). Thereby, the position in the height direction of the optometry window can be adjusted according to the arrangement position of the subject's eye. For example, the vertical movement mechanism 313L is provided with a known configuration using a drive means and a driving force transmission means that transmits driving force generated by the drive means, receives a control signal from a control device (not shown) and moves the left inspection unit 320L in the up-down direction. The vertical movement mechanism 313L is capable of moving the left inspection unit 320L in the up-down direction manually under reception of the operation by the operator.

The vertical movement mechanism 313R moves the right inspection unit 320R in the up-down direction. Thereby, the position in the height direction of the optometry window can be adjusted according to the arrangement position of the subject's eye. The vertical movement mechanism 313R may move the right inspection unit 320R in conjunction with the movement by the vertical movement mechanism 313L or may move the right inspection unit 320R independently of the movement by the vertical movement mechanism 313L. The vertical movement mechanism 313R has the same configuration as the vertical movement mechanism 313L, receives a control signal from a control device (not shown) and moves the right inspection unit 320R in the up-down direction. The vertical movement mechanism 313R is capable of moving the right inspection unit 320R in the up-down direction manually under reception of the operation by the operator.

The left inspection unit 320L and the right inspection unit 320 are individually operable.

According to such an ophthalmological inspection system, the subjective inspection or the objective measurement for both eyes can be easily performed.

(Actions and Effects)

The actions and effects of the ophthalmological device and the ophthalmological inspection system according to the embodiments will be described.

An ophthalmological device according to the embodiments comprises an objective lens (objective lens 51), an objective measurement optical system (a part of refractometry projection system 6, refractometry light reception system 7, and the observation system 5), an interference optical system (OCT optical system 8), and an image forming unit (image forming unit 122). The objective measurement optical system irradiates light onto a subject's eye (subject's eye E) via the objective lens and detects returning light from the subject's eye. The interference optical system splits light (light LO) from a light source (OCT light source 91) into reference light (reference light LR) and measurement light (measurement light LS), projects the measurement light onto the subject's eye via the objective lens so as to overlap at least part of an area of the irradiated light at the subject's eye by the objective measurement optical system, generates interference light (interference light LC) between returning light of the measurement light and the reference light, and detects the generated interference light. The image forming unit forms a tomographic image of the subject's eye based on a detection result of the interference light by the interference optical system.

According to such a configuration, the tomographic image of the subject's eye can be formed by irradiating the measurement light via the objective lens so as to overlap at least part of the area of the light for the objective measurement irradiated onto the subject's eye and by detecting the interference light based on the returning light thereof. Thereby, since it is possible to acquire the tomographic image at the vicinity of the irradiated area of the light for the objective measurement, the accuracy of the objective measurement values obtained by the objective measurement can be improved by observing the relationship between the objective measurement result and the tomographic image. For example, when it is judged that there is a problem in the objective measurement result, it is possible to assist in judging whether the cause is in the fundus or in the ocular media including the crystalline lens, or the like, by observing the tomographic image and judging the presence or absence of abnormality of the fundus.

Further, the ophthalmological device according to the embodiments may further comprise an attention site specifying unit (site specifying unit 124) that specifies an attention site of the subject's eye based on the returning light from the subject's eye detected by the objective measurement optical system, wherein the interference optical system may irradiate the measurement light to the attention site specified by the attention site specifying unit.

According to such a configuration, since the attention site is specified from the returning light from the subject's eye detected by the objective measurement optical system and the measurement light is irradiated onto the specified attention site, it is possible to easily acquire the tomographic image at a site to be paid attention to in the objective measurement.

Further, in the ophthalmological device according to the embodiments, the objective measurement optical system may project a ring-shaped measurement pattern onto a fundus (fundus Ef) of the subject's eye, and the attention site specifying unit may specify the attention site based on a pattern image on the basis of the returning light from the fundus.

According to such a configuration, since the attention site is specified based on the pattern image on the basis of the returning light of the ring-shaped measurement pattern projected onto the fundus of the subject's eye, it is possible to easily specify a site to be paid attention to in the objective refractive power measurement, for example.

Further, in the ophthalmological device according to the embodiments, the attention site specifying unit may specify the attention site based on a detection result of the interference light.

According to such a configuration, since the attention site is specified based on the detection result of the interference light based on the returning light of the measurement light irradiated onto the subject's eye, it is possible to easily specify a site to be paid attention to in the objective refractive power measurement, for example.

Further, in the ophthalmological device according to the embodiments, the interference optical system may include an optical scanner (optical scanner 84) that deflects the measurement light, and the ophthalmological device may further comprise a controller (controller 110) that controls the optical scanner to scan the attention site specified by the attention site specifying unit with the measurement light.

According to such a configuration, since the optical scanner is controlled so as to scan a site to be paid attention to in the objective measurement with the measurement light, it is possible to easily acquire a tomographic image at the vicinity of the site to be paid attention to in the objective measurement such as the objective refractive power measurement or the like. Further, since the scan is performed on the specified attention site, the scan time can be greatly shortened.

Further, in the ophthalmological device according to the embodiments, the controller may control the optical scanner so as to scan the attention site with the measurement light in a radial shape or a circle shape.

According to such a configuration, since the tomographic image at the attention site by the radial scan or the circle scan, it is possible to judge the objective measurement result based on the tomographic image at the site where the objective measurement is performed.

Further, the ophthalmological device according to the embodiments may further comprise a display controller (display controller 111A) that controls a display unit to display an image based on the returning light of the light irradiated by the objective measurement optical system, wherein the display controller may control the display unit to identify and to display the attention site specified by the attention site specifying unit.

According to such a configuration, since the attention site is displayed so as to identify the site, it is possible to assist in improving the accuracy of the objective measurement.

Further, the ophthalmological device according to the embodiments may further comprise an ocular refractive power calculator (ocular refractive power calculator 121) that calculates a refractive power of the subject's eye based on the returning light from the subject's eye detected by the objective measurement optical system, wherein the ocular refractive may calculate a new refractive power by deleting or interpolating a measurement result at the attention site acquired by the objective measurement optical system and calculating again the refractive power of the subject's eye.

Here, the measurement result acquired by the objective measurement optical system may be a detection result of the returning light from the subject's eye detected by the objective measurement optical system or a calculation result such as the objective measurement value generated based on the detection result, etc. According to such a configuration, since the calculation of the new refractive power is performed by deleting or interpolating the measurement result at the attention site, it is possible to acquire the refractive power of the subject's eye which is not affected by the measurement result at the abnormal site such as the diseased site or the like. Thus, the accuracy of the objective measurement value acquired by the objective measurement can be improved.

Further, an ophthalmological inspection system according to the embodiments may comprise a left inspection unit for inspecting the subject's left eye and a right inspection unit for inspecting the subject's right eye, wherein at least one of the left inspection unit and the right inspection unit includes the ophthalmological device described above.

According to such a configuration, it is possible to provide the ophthalmological inspection system which is capable of improving the accuracy of the objective measurement value for both eyes with a simple configuration.

Other Modification Examples

The above-described embodiment is merely an example for carrying out the present invention. Those who intend to implement the present invention can apply any modification, omission, addition, or the like within the scope of the gist of the present invention.

In the above embodiments or the modification examples thereof, the case has been described in which the optical scanner 84 is controlled so as to scan the projection site of the ring-shaped light flux projected onto the fundus Ef. However, the configuration of the ophthalmological device according to the embodiments or the modification examples thereof is not limited thereto. For example, light flux for measurement may be projected onto the anterior ocular segment of the subject's eye E and the optical scanner 84 may be controlled so as to scan this projection site.

In the above embodiments or the modification examples thereof, an image rotator capable of rotation around the optical axis of the OCT optical system 8 may be provided instead of the galvano mirror 84Y.

In the above embodiments or the modification examples thereof, the cases that the interference optical system is configured to perform OCT imaging are described. However, the interference optical system may be configured to perform OCT measurement. For example, the interference optical system may be configured to perform measurement of the axial length of the eye, the corneal thickness, the anterior chamber depth, the crystal thickness, or the like.

It is possible to apply the invention according to the above embodiments to apparatuses having arbitrary functions adaptable in the field of ophthalmology. Examples of such functions include a tonometry function, a fundus photography function, an anterior ocular segment photography function, an optical coherence tomography (OCT) function, an ultrasonic examination function, and the like. The tonometry function is realized by a tonometer or the like. The fundus photography function is realized by a fundus camera, a scanning laser ophthalmoscope (SLO) or the like. The anterior ocular segment photography function is realized by a slit lamp microscope or the like. The OCT function is realized by an optical coherence tomography apparatus or the like. The ultrasonic examination function is realized by an ultrasonic diagnostic apparatus or the like. Further, the present invention can also be applied to an apparatus (multifunctional apparatus) having two or more of such functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ophthalmological device comprising:
an objective lens;
an objective measurement optical system that irradiates light onto a subject's eye via the objective lens and detects returning light from the subject's eye;
an interference optical system that splits light from a light source into reference light and measurement light, projects the measurement light onto the subject's eye via the objective lens, generates interference light between returning light of the measurement light and the reference light, and detects the generated interference light;
an image forming circuit that forms a tomographic image of the subject's eye based on a detection result of the interference light by the interference optical system;
an attention site specifying circuit that specifies an attention site of the subject's eye based on the returning light from the subject's eye detected by the objective measurement optical system; and
an ocular refractive power calculator that calculates a refractive power of the subject's eye based on the returning light from the subject's eye detected by the objective measurement optical system, wherein
the ocular refractive power calculator calculates the refractive power of the subject's eye based on a ring image obtained by deleting or interpolating a measurement result at the attention site acquired by the objective measurement optical system.

2. The ophthalmological device of claim 1, wherein
the interference optical system irradiates the measurement light to the attention site specified by the attention site specifying circuit.

3. The ophthalmological device of claim 2, wherein
the objective measurement optical system projects a ring-shaped measurement pattern onto a fundus of the subject's eye, and
the attention site specifying circuit specifies the attention site based on a pattern image on the basis of the returning light from the fundus.

4. The ophthalmological device of claim 3, wherein
the interference optical system includes an optical scanner that deflects the measurement light, and
the ophthalmological device further comprises a controller that controls the optical scanner to scan the attention site specified by the attention site specifying circuit with the measurement light.

5. The ophthalmological device of claim 4, wherein
the controller controls the optical scanner so as to scan the attention site with the measurement light in a radial shape or a circle shape.

6. The ophthalmological device of claim 2, wherein
the attention site specifying circuit specifies the attention site based on a detection result of the interference light.

7. The ophthalmological device of claim 6, wherein
the interference optical system includes an optical scanner that deflects the measurement light, and
the ophthalmological device further comprises a controller that controls the optical scanner to scan the attention site specified by the attention site specifying circuit with the measurement light.

8. The ophthalmological device of claim 7, wherein
the controller controls the optical scanner so as to scan the attention site with the measurement light in a radial shape or a circle shape.

9. The ophthalmological device of claim 2, further comprising:
a display controller that controls a display to display an image based on the returning light of the light irradiated by the objective measurement optical system, wherein
the display controller controls the display to identify and to display the attention site specified by the attention site specifying circuit.

10. An ophthalmological inspection system comprising:
a left inspection unit for inspecting the subject's left eye; and
a right inspection unit for inspecting the subject's right eye, wherein
at least one of the left inspection unit and the right inspection unit includes the ophthalmological device of claim 2.

11. An ophthalmological inspection system comprising:
a left inspection unit for inspecting the subject's left eye; and
a right inspection unit for inspecting the subject's right eye, wherein
at least one of the left inspection unit and the right inspection unit includes the ophthalmological device of claim 1.

* * * * *